United States Patent
Ciamacco, Jr.

(10) Patent No.: US 8,936,632 B2
(45) Date of Patent: Jan. 20, 2015

(54) STENT DELIVERY AND DEPLOYMENT SYSTEM

(76) Inventor: Sam Ciamacco, Jr., San Diego, CA (US)

(*) Notice: Subject to any disclaimer, the term of this patent is extended or adjusted under 35 U.S.C. 154(b) by 0 days.

(21) Appl. No.: 12/364,504

(22) Filed: Feb. 2, 2009

(65) Prior Publication Data
US 2009/0198317 A1  Aug. 6, 2009

Related U.S. Application Data

(63) Continuation-in-part of application No. 10/269,762, filed on Oct. 10, 2002, now Pat. No. 7,485,139.

(51) Int. Cl.
| | | |
|---|---|---|
| *A61F 2/06* | (2013.01) | |
| *A61M 29/00* | (2006.01) | |
| *A61F 2/856* | (2013.01) | |
| *A61F 2/86* | (2013.01) | |
| *A61F 2/958* | (2013.01) | |
| *A61F 2/844* | (2013.01) | |
| *A61F 2/82* | (2013.01) | |
| *A61M 25/01* | (2006.01) | |

(52) U.S. Cl.
CPC . *A61F 2/856* (2013.01); *A61F 2/86* (2013.01); *A61F 2/958* (2013.01); *A61F 2/844* (2013.01); *A61F 2002/826* (2013.01); *A61M 2025/0183* (2013.01)
USPC ............... 623/1.11; 623/1.15; 606/198

(58) Field of Classification Search
CPC ........... A61F 2/86; A61F 2/844; A61F 2/856; A61F 2/985; A61F 2002/826; A61M 2025/0183
USPC ........ 606/191, 194, 198; 623/1.11, 1.15, 1.16
See application file for complete search history.

(56) References Cited

U.S. PATENT DOCUMENTS

| | | | |
|---|---|---|---|
| 4,723,936 A * | 2/1988 | Buchbinder et al. | 604/95.01 |
| 6,231,598 B1 * | 5/2001 | Berry et al. | 623/1.15 |

* cited by examiner

*Primary Examiner* — Tuan V Nguyen
(74) *Attorney, Agent, or Firm* — Donn K. Harms

(57) ABSTRACT

A stent delivery and deployment system for placement of vascular stents having apertures therein for deployment at intersecting blood vessels. The device employs a guide wire having an angled distal end which is threaded into position at the intersection of a first blood vessel and second blood vessel. With the angled portion of the guide wire threaded into the intersecting blood vessel, the stent may be translated along the guide wire to easily position the aperture in line with the intersecting blood vessel.

3 Claims, 3 Drawing Sheets

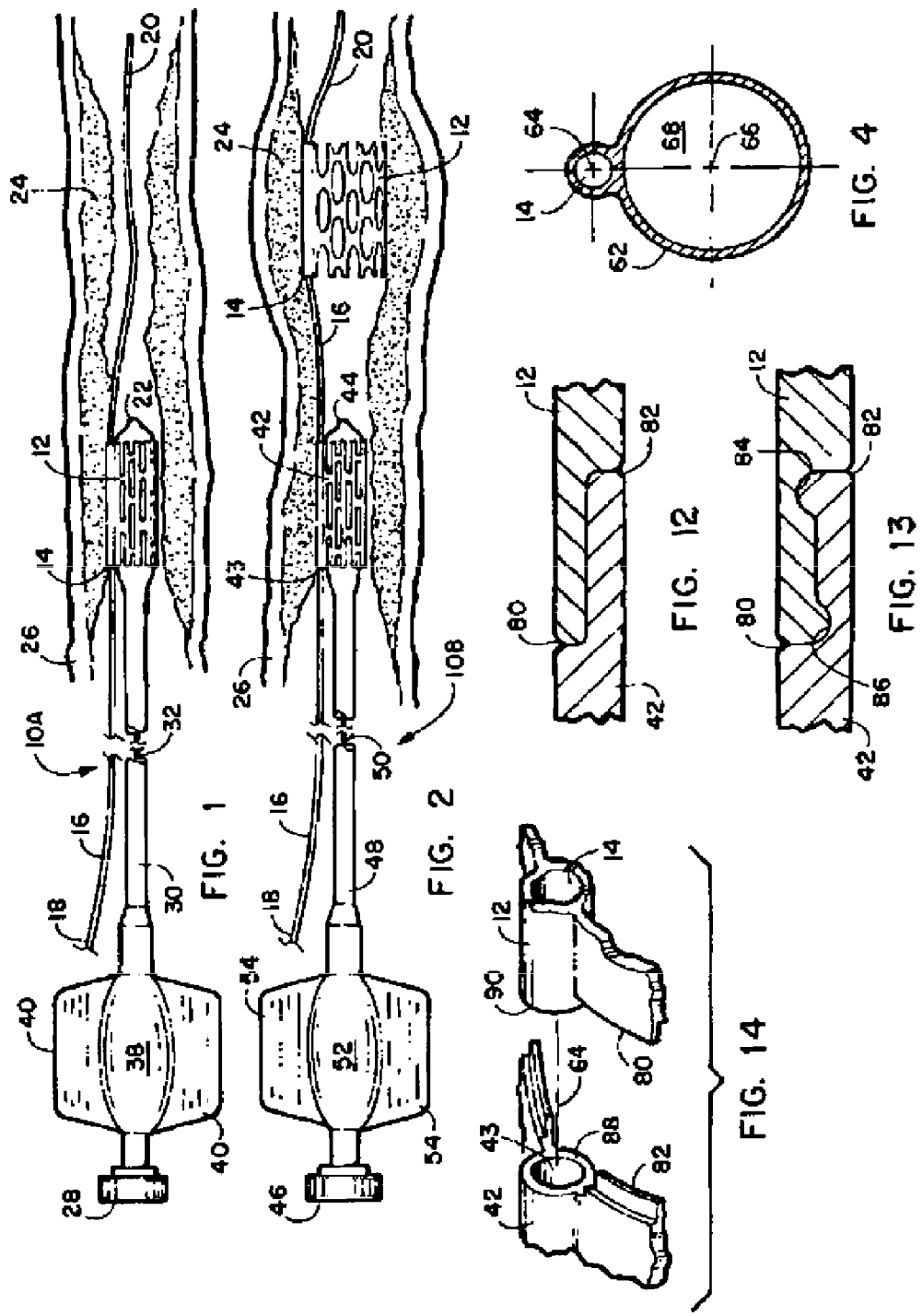

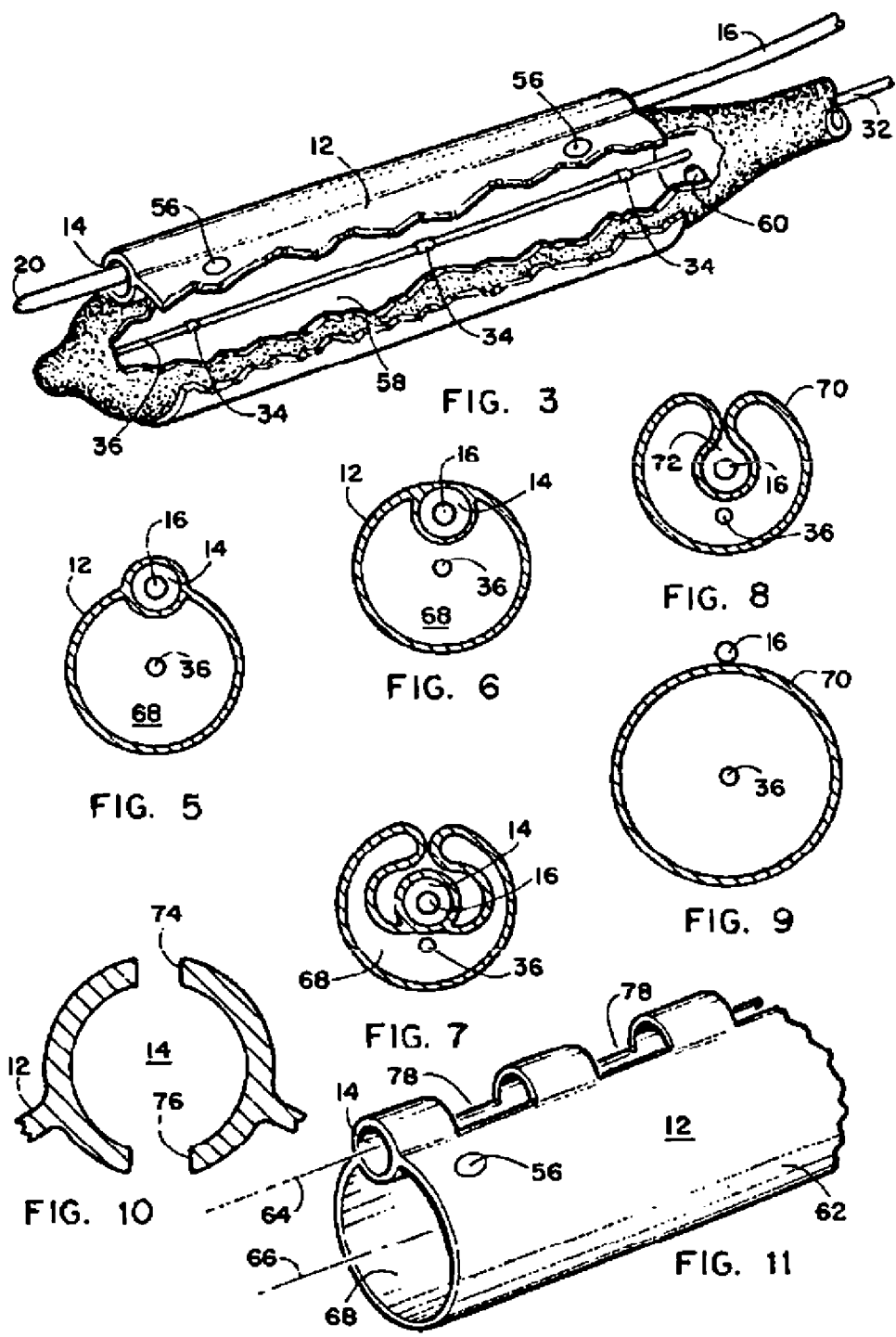

STENT DELIVERY AND DEPLOYMENT SYSTEM

This application is a Continuing in Part of U.S. patent application Ser. No. 10/269,762 filed on Oct. 10, 2002 now U.S. Pat. No. 7,485,139 and incorporated by reference herein in its entirety.

FIELD OF THE INVENTION

The present invention relates to the field of angioplasty. More particularly, the disclosed device provides for the insertion, delivery and deployment of one or a plurality of stents into the arterial or venal system of the human body which also has unique abutment, overlapping and interlocking capabilities provided by guiding the stent to position using a single in-place guide wire. Additionally, the device provides for the addition of one or more stents with or without overlapping or interlocking capabilities adjacent to an existing implanted stent within the arterial or venal system of the human body.

BACKGROUND OF THE INVENTION

The use of balloon angioplasty catheters to treat strictures, stenoses, or narrowing of the arterial or venal system within various parts of the human body is well known. In a typical procedure, for example, to dilate a blockage or stenosis in the coronary or other arteries in the body, conventionally a relatively large guiding catheter is inserted into the patients' arterial system in the groin. The guiding catheter is then advanced through the arteries to a location near the patients' heart by the means of a radiopaque marker system. A small guide wire is then inserted within the guiding catheter and advanced to the distal end of the guiding catheter, at which point the wire is extended from the distal end of the guiding catheter and steered to extend through the stenosis in the coronary arteries. Once the distal end of the wire is properly positioned by the surgeon, a balloon angioplasty catheter is then advanced into and through the guiding catheter and over the guide wire until the deflated balloon lays across the stenosis. A working fluid is then pumped through the balloon angioplasty catheter, thereby inflating the balloon and dilating the passage through the stenosis.

After such a dilatation procedure, it is often found desirable to install a stent in the area of the stenosis in order to insure patency of the lumen in the artery. Such a stent is generally delivered to the site using the same path as the prior inserted balloon catheter by insertion into, and threading through the guiding catheter, on the end of an inflatable balloon stent delivery catheter. The expandable stent is collapsed around the deflated balloon of the balloon delivery catheter and the catheter is inserted into the patients' body to the location of the stenosis. When the balloon of the stent delivery catheter is inflated, the stent is plastically deformed to an expanded condition to maintain the passage through the stenosis in a dilated condition. Once the stent is expanded, the balloon is deflated, and the stent delivery catheter is withdrawn from the guiding catheter, leaving the expanded stent in place to preserve the patency of the arterial lumen.

Because such conventional stent delivery catheters have a guide wire lumen which extends the entire length of the catheter, they cannot be inserted to the stenosis site over the guide wire that is used to insert the balloon angioplasty catheter (such guide wires are too short). Therefore, after the stenosis has been dilated by inflation of the balloon, the balloon angioplasty catheter and guide wire must be removed from the guiding catheter and a second guide wire, or exchange guide wire, must be inserted through the guiding catheter and steered to the stenosis location. The exchange guide wire is generally more than twice as long as the stent delivery catheter because it is necessary that the guide wire protrude from the patients' body by the length greater than the length of the stent delivery catheter. This allows the guide wire to be held steady with the physician's hand while the stent delivery catheter is advanced over the guide wire. Once the distal end of the stent delivery catheter has been placed within the area of the dilated stenosis, the balloon of the stent delivery catheter may be inflated, thereby plastically deforming the stent in the region of the dilated stenosis. The balloon of the stent delivery catheter is then deflated, allowing the stent delivery catheter to be withdrawn, leaving the expanded stent in place. The exchange guide wire and the guiding catheter are then withdrawn, thereby completing the operation.

In situations where physicians find it desirable to install a stent after the balloon angioplasty procedure, the need to replace the guide wire with an exchange guide wire is a cumbersome and undesirable requirement. This is due to the fact that it is necessary that the second guide wire be steered through the patients' arterial system until it reaches the location of the original stenosis. Furthermore, the great length of the exchange guide wire that extends outside the patients' body must sometimes extend beyond the sterile area of the surgical table.

Additionally, physicians find that some stenoses are too long for a single stent insertion and more than one stent is required to complete the procedure, requiring a gap between each stent. This gap has been found to be undesirable and a possible location where an additional stenosis may develop. Scaffolding the artery wall from inside the lumen to achieve wide and stable patency is an old concept. Several types of stents (coil, mesh, or cage type and metallic or polymer) have been invented and are in use in experimental and clinical procedures. Early application of a stent after the occurrence of occlusion and/or dissection decreases the need for emergency bypass surgery and the risk for myocardial infarction (MI). Most stents currently available for coronary artery disease or neurovascular or other blood vessel blockages are balloon expandable. Some of them require a protective sheath to avoid dislodgement of the stent from the balloon. Because of their large profile, stent/balloon combinations require larger catheters and accordingly larger adapters and sheaths. To facilitate passage of the balloon through tortuous proximal vessels, stiffer angioplasty guide wires are used.

The device as herein disclosed describes a new and unique stent delivery and deployment system that consists of a guide wire cavity incorporated into the conventional stent but separate from the central tubular cavity. More particularly, this device discloses the capabilities of a stent which can be made to abut, overlap, interlock or otherwise communicate with either side of a stent that has been previously inserted, without removing the guide wire and without the need for a guide wire lumen or catheter to be initially inserted. This is accomplished by removing the balloon angioplasty catheter after deflation from the patient with the initial stent in place without removing the guide wire, then by inserting the guide wire from the proximal end into the guide wire cavity of the second stent and inserting the second balloon angioplasty catheter and stent into the patient as previously described. The stents may be brought together in substantially perfect alignment by means of the guide wire not being removed from the initial stent and the second stent brought to full alignment and engagement with the guide wire captive within the guide wire cavities of both stents, with the results checked by the means of a radiopaque marker system.

The convenience and economy of this device can be described by the ability of maintaining the sterility of the device, not requiring the great length of the exchange guide wire that extends outside the patients' body often required, and the ability of maintaining control of the device during the procedure. Having the guide wire in place, without removal until the procedure is completed, the physician has the ability to verify that the procedure has been completed correctly and negating any reinsertion of either additional guide lumens, guide wires, or balloon catheters into the patient.

U.S. Pat. No. 4,824,435 of Jerry D. Giesy et al. describes an instrument guidance system of elongated flexible elements that are guided into place within a tortuous body passage by providing the elements with annular guides adjacent their distal ends and sliding the elements over a guide wire extended through the passage. The '435 patent describes a guidance system, but does not take into account the use of a stent or the delivery or deployment thereof.

U.S. Pat. No. 5,690,642 of Thomas A. Osborne teaches of a rapid exchange stent delivery balloon catheter, which allows exchange from a balloon angioplasty catheter to a stent delivery catheter without the need to replace the angioplasty catheter guide wire with an exchange-length guide wire before exchanging the stent delivery catheter for the balloon angioplasty catheter. The stent delivery catheter of this invention includes a relatively short guide wire shaft, which is bonded to the catheter shaft only at a location distal to the inflation lumen. Although the '642 patent eliminates the need for the exchange-length guide wire, it provides no means to engage a second stent without removing the angioplasty catheter guide wire and restarting the procedure.

U.S. Pat. No. 6,413,269 of Dennis Bui et al. tells of a stent delivery catheter. The catheter includes an inner tube and an outer tube, which are rotatable relative to each other. The inner catheter and the outer catheter include recesses to receive the ends of the stent, permitting pull wires to engage the stent ends without need for the pull wires to extend radially beyond the bounds of the catheter or requiring the stent ends to protrude into the lumen of the inner or outer catheter. This '269 patent deals with the manipulation of the conventional stent and does not incorporate the unique feature of the guide wire passage as an integral part of the stent structure.

U.S. Pat. No. 5,810,871 of Joel F. Tuckey et al. discloses a stent delivery system comprising an inflation shaft having an expandable balloon sealingly mounted at the distal end thereof and a tubular sheath having the inflation shaft longitudinally running therethrough. The tubular sheath has an expandable sheath at the distal end thereof with the balloon longitudinally running therethrough and an expandable stent mounted on the expandable sheath. This is another patent that is designed specifically for the insertion of a single stent and if a second is required, the procedure must be repeated without the ability of joining the stents together.

U.S. Pat. No. 6,015,429 of Lilip Lau et al. describes a foldable stent or stent-graft, which may be per cutaneously delivered with or on a catheter, typically an endovascular catheter, to a body cavity of lumen and then expanded. The expandable stent structure utilizes torsional members that distribute bending and folding loads is such a way that the stent is not plastically deformed. The '429 patent deals primarily with the structure of the segmented shapes of the stent with the ability of lacing it together prior to insertion. It does not incorporate a guide wire channel and does not describe the overlapping or interlocking capabilities.

U.S. Pat. No. 6,048,361 of Randolf Von Oepen teaches of a device for implanting into a body vessel in the region of a vessel branching has a radially expandable stent formed as a hollow cylindrical element and provided with an increased radial opening. The '361 patent describes a unique design of a stent with an opening on the side to be applied at the juncture of a vessel allowing the blood to flow to the side through the opening. It does not describe a stent with the guide wire passage and the overlapping or interlocking capabilities.

U.S. Pat. No. 6,071,285 of Robert D. Lashinski describes a balloon portion of a balloon catheter for implanting a stent structure that is at least initially retained laterally to a guide wire by passing the guide wire axially along the balloon inside the stent structure but not through the interior of the balloon or any permanent guide wire lumen at the location of the balloon. The '285 patent is another patent designed for the implantation of a single stent whereby if another stint is required the procedure must be repeated due to the fact that the guide wire feeds in and out of the balloon catheter lumen along with the fact that there is no adaptation for the overlapping or interlocking of additional stents.

U.S. Pat. No. 6,270,521 of Robert E. Fischell teaches of a stent delivery system for placing a stent within a stenosis in a vessel of a human body without the need for pre-dilation of the stenosis or post-dilation of the stent. This design makes it possible for the stent delivery catheter to be pushed through even very tight stenosis without requiring pre-dilation. This '521 patent deals with the delivery and application of a single stent with no means of inserting a second without removal of the device and repeating the process, and no means of joining two or more stents in the same operation without removing the guide wire.

U.S. Pat. No. 6,409,754 of Scott R. Smith et al. describes a radially expandable segmented stent having plastic, i.e., permanent deformation, with connectors interlocking each segment. This patent deals with the design and segmentation of a conventional cylindrical stent, not with the incorporation of an additional guide wire cavity or the overlapping or interlocking capabilities of the herein disclosed patent.

U.S. Pat. No. 6,409,761 of G. David Jang discloses another patent with the unique patterns in the fabrication of stents endeavoring to make the stints expandable without shortening the initial length. They do not relate to the delivery system or the engagement of two or more stents together.

U.S. Pat. No. 6,423,092 of Arindam Datta tells of a biodegradable stent that is unique, but does not relate to the soindesclosed patent.

Consequently there exists a need field of angioplasty, for a stent delivery and deployment system, which will allow physicians to insert a guide wire after which one or more stents with interlocking capabilities may be inserted into a stenosis in the arterial or venal system of the human body.

SUMMARY OF THE INVENTION

This invention relates to the insertion, delivery and deployment of one or more stents into the arterial or venal system of the human body. In particular, this invention relates to the incorporation of a unique guide wire passage into the structure of the conventional stent whereby the guide wire can be inserted and the stent slidably engaged on the guide wire becomes the guide means to transport one or more balloon angioplasty catheters into the area of the stenosis. Using the stent slidably engaged on the guide wire also eliminates the need for a guide wire lumen.

The preferred embodiment of this invention consists of a stent that, when in the expanded state, will form a tubular central cavity and a secondary guide wire passage as a means of transporting the stent and balloon angioplasty catheter into the desired position. The varying segmentation of the stent structure is a common practice to insure that the length of the stent does not change after it has been expanded. The so disclosed guide wire passage can be continuous or segmented latterly or transversely, it also can be wire formed or die cut, as long as it maintains the configuration that will retain the guide wire during the insertion, delivery and deployment of the stent and balloon catheter. Upon completion of the process the guide wire passage can work as a secondary cavity to the stent central cavity for the transportation of blood. The combination of both the guide wire passage and the stent central cavity becomes a strengthening member along the length of the stent. Additionally, when a stenosis is hard and difficult to expand, the guide wire passage located axially adjacent to the stents' central cavity produces a point where, along the length of the stent, the pressure is concentrated to crack the stenosis in a line parallel to the vessel.

The principle of this invention is that there is a separate tubular guide wire passageway formed on the stent substantially parallel to the tubular stent central cavity incorporated into the design structure of the stent. This passageway provides for engagement of the stent with the pre-positioned guide wire. With the stent engaged with a catheter or other means to translate it along the guide wire, the stent becomes a means to track and guide the inserted device attached to it, such as a balloon catheter, and eliminates the need for the guiding catheter and other parts conventionally used. A preferred embodiment of the invention will have the guide wire passage in a coaxial position when the balloon angioplasty catheter and stent are in a compressed state. When the stent is in the expanded condition, the guide wire passage can be located either completely out of the stent central cavity, half in and half out of the stent central cavity, or completely within the central cavity of the stent and still be covered within the scope of this patent. Or, as those skilled in the art will see, the guide wire passage may be located any percentage in and out of the central cavity as the design and use permits and dictates and such is anticipated.

A secondary feature of this invention is the unique capability of the distal end of the stent being able to overlap or interlock with the proximal end of a previously implanted stent without removal of the guide wire. Overlapping of two or more stents is accomplished by the means of relieving the inner surface of material on the distal ends, and relieving the outer surface of material on the proximal ends of the stents. The means of interlocking of the stents is accomplished by under cutting the inner surface at the adjoining end of one stents, and under cutting the outer surface on the adjacent end of the adjacently placed stents. Additionally, the guide wire passage can be stepped in on the distal end of the stent and stepped out on the proximal end of the stent, adding to the exact alignment and nesting of one stent into another.

Markers used in the conventional proximal radiopaque marker system that are normally located as bands along the distal end of the guide lumen for locating its exact location will be located at the distal and proximal ends of the stent central cavity or the guide lumen cavity to aide in the positioning of the stents, but are not needed for alignment.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent construction insofar as they do not depart from the spirit and scope of the present invention.

The object of this stent delivery and deployment system is to create a means to translate a stent and balloon angioplasty catheter over a guide wire into a determined position to stenosis within a blood or other fluid carrying vessel of a patient by a physician or surgeon.

Another object of this stent delivery and deployment system is to translate one or a plurality of additional stents and balloon angioplasty catheter over the same guide wire into an extended stenosis within a vessel of a patient by a physician or surgeon without the need to remove the guide wire.

Yet another object of this stent delivery and deployment system is to guarantee that each additional stent inserted along the guide wire is held in substantially perfect alignment with the preceding stent.

A further object of this stent delivery and deployment system is to provide the ability for overlapping, interlocking, or other means to cooperatively engage two adjacent stents together.

Still another object of the stent delivery and deployment system is to have the ability of interlocking two or more adjacent stents either consecutively or all at once.

Another object of this invention is to provide a system for physicians and surgeons to be able to treat a stenosis that exceeds the length of conventional existing stents without having a gap between multiple stents and having those stents form an integral structure.

Yet another object of this invention is the provision of a stent configured for bifucated flow with an intersecting blood vessel from a primary blood vessel.

These together with other objects and advantages which become subsequently apparent reside in the details of the construction and operation as more fully hereinafter described and claimed, reference being made to the accompanying drawings forming a part thereof, wherein like numerals refer to like parts throughout.

BRIEF DESCRIPTION OF THE DRAWINGS

The accompanying drawings, which are incorporated in and form a part of this specification, illustrate embodiments of the invention and together with the description, serve to explain the principles of this invention.

FIG. 1 depicts a section of a body vessel with a stenosis longer than a conventional stent located on the guide wire, with the stent in the compressed state prior to its expansion.

FIG. 2 depicts a section of a vessel with a stenosis longer than a conventional stent, the first stent expanded in place with the guide wire still located in the guide wire passage, and the second stent and balloon catheter and stent on the same guide wire, approaching the first stent.

FIG. 3 is a perspective view of a conventional stent with proximal radiopaque markers with the guide wire passage and a guide wire within, and a typical balloon catheter and stiffening wire with proximal radiopaque marker bands.

FIG. 4 is an end view of the proposed stent with the guide wire passage on the exterior surface.

FIG. 5 is an end view of the proposed stent with the guide wire passage half in and half out of the stent central cavity.

FIG. 6 is an end view of the proposed stent with the guide wire passage completely within the stent central cavity.

FIG. 7 is an end view of a compressed stent so that the guide wire passage is in a coaxial position with relation to the outer diameter of the stent.

FIG. 8 is an end view with the outer surface of the stent forming the guide wire passage and the guide wire in a coaxial state with the outer diameter of the collapsed stent.

FIG. 9 is an example of the location of the guide wire when the stent does not have a guide wire passage.

FIG. 10 is an end view of bilateral segmentation of the guide wire passage.

FIG. 11 is a perspective view of a stent with a transversely segmented guide wire passage.

FIG. 12 is a section through the side wall of two conventional stents with the distal end on one relieved on the outside, and the proximal end on the other relieved on the inside in an overlapping position.

FIG. 13 is a section through the sidewall of two conventional stents with the distal end on one undercut on the outside and the proximal end of the other undercut on the inside in an interlocking position.

FIG. 14 is a perspective view of the guide wire passage stepped in on the distal end of one stent and the guide wire passage stepped out on the proximal end of another stent approaching a nesting position.

DETAILED DESCRIPTION OF THE PREFERRED EMBODIMENTS

Figure 15:
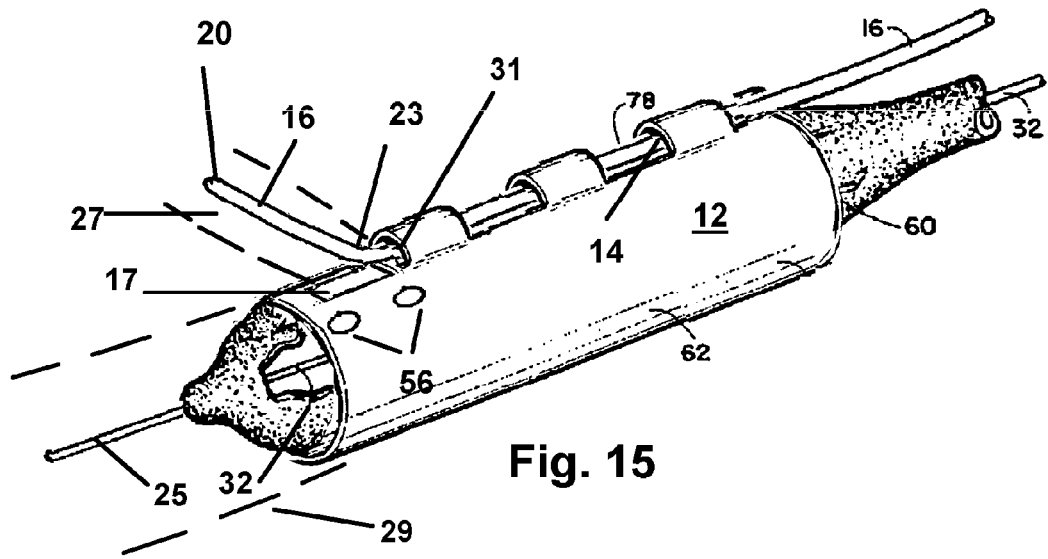
FIG. 15 depicts another mode of the device herein configured for a deployment aligned with an intersecting blood vessel with or without a secondary stent.

Referring now to the drawings FIG. 1-16, wherein similar parts of the invention are identified by like reference numerals, there is seen in FIG. 1 a first preferred embodiment of the stent delivery and deployment system 10A. The device depicted consists of a stent 12 with the guide wire passage 14 formed integral to or upon a wall surface of the stent 12. The guide wire passage 14 engages and translates the stent 12 over the guide wire 16 extending from outside the patients' body at the guide wire's proximal end 18, through the arterial or venal system of the patient, to the guide wire distal end 20. The stent 12 is shown operatively engaged on the balloon angioplasty catheter 22 within an elongated arterial stenosis 24 within a typical blood vessel 26 such as a coronary artery, vein, or neurovascular blood vessel of a patient. The balloon angioplasty catheter 22 as shown provides a means to laterally translate stent with the guide wire 16 engaged through the guide wire passage 14 to the proper position. The balloon angioplasty catheter 22 is connected to the inflation port 28 by the means of an inflation lumen 30. A saline solution or other inflation media, is inserted into the inflation port 28 and communicated to the interior of the distal end of the balloon angioplasty catheter 22 to expand the balloon angioplasty catheter 22 and thereby expand the first stent 12 mounted thereon. This expansion provides a means to expand the stent 12 to a fixed engagement between and exterior surface of the stent 12 and an interior surface of the blood vessel 26.

It should be also noted that since the stent 12 is engaged with the guide wire 16 the stent 12 can act as the steering mechanism to a wide variety of conventional and new catheters, wires, and other flexible elongated devices. This would be accomplished by making the stent 12 cooperatively engageable with the distal end of one or a plurality of such elongated devices and attaching the proper device for the job at hand to the stent 12 intended for placement. Currently the means for cooperative engagement to the catheter providing the means for lateral translation of the stent 12 on the guide wire 16 is the enlargeable distal end of the balloon angioplasty catheter 22. However, other means of cooperative engagement such as frictional engagement or threads or other frictional engagements are anticipated so long as the stent 12 is removably mounted to the distal end of the device used to laterally translate it on the guide wire 16 to its determined position in a blood vessel 26.

A stiffening wire 32 runs the complete length of the inflation lumen 30 and the balloon angioplasty catheter 22. The stiffening wire 32 located within the inflation lumen 30 and the balloon angioplasty catheter 22 in the current best mode of the device has a plurality of marker bands 34 located on the distal end 36 within the balloon angioplasty catheter 22 for determining the exact location of the first stent 12 and the balloon angioplasty catheter 22 using the a radiopaque marker detection system. The inflation port 28 is coupled to a bulbous unit 38 with the set of adjusting tabs 40 to be used by the physician to manipulate the stent delivery and deployment system 10 within the area of the stenosis 24.

FIG. 2 depicts the second stent delivery and deployment system 10B in a section of a blood vessel 26 with an arterial stenosis 24, which exceeds the length of the first placed stent 12. The stent 12 first positioned in the blood vessel 26, having been expanded in place, still has the guide wire 16 located in the guide wire passage 14 of the stent 12. A second stent 42 and second balloon angioplasty catheter 44 are shown with the guide wire 16 translating through the second guide wire passage 43, and approaching the first stent 12. The second stent delivery and deployment system 10B is located in close proximity to the first stent 12 having been expanded by inflation from injection of an inflation media such as a saline solution in the inflation port 46. The second balloon angioplasty catheter 44 is connected to the second inflation port 46 by the means of the second inflation lumen 48. An inflation media is again pumped into the inflation port 46 to expand the second balloon angioplasty catheter 44 and expand the stent 42. As the second stent 42 is expanded may be nested with the first expanded stent 12. A second stiffening wire 50 runs the complete length of the second inflation lumen 48 and the second balloon catheter 44. The second inflation port 46 is coupled to the second bulbous unit 52 with the second set of adjusting tabs 54 to be used by the physician to manipulate the second stent delivery and deployment system 10B in place.

As shown, the stent delivery systems 10A and 10B both provide a means to laterally translate the stent 12 on the guide wire 16 to the proper placement in the blood vessel 26. Of course those skilled in the art will recognize that other means to translate the stent 12 along its slidable engagement with the guide wire 16 might be used or developed, especially in light of the benefits and options provided by the device herein disclosed, and all such substitutions and modifications are anticipated. As noted, the stent 12 and guide wire 16 engagement eliminate the need for the placement of a wire guiding lumen or catheter as well as an exchange wire that is twice the length of the stent delivery catheter. This will allow for the use of the device herein disclosed in narrower blood vessels than previously possible. Further, it eliminates the concerns of the medical staff regarding the clumsy engagement of the conventional long exchange wire with stent delivery catheter and possibly violating the sterile field from the long exchange wire hitting the floor or other non-sterile areas. This is because the guide wire 16 of the disclosed device need only extend a very short distance from the patient to allow the engagement of the guide wire passage 14 over the guide wire 16 and the subsequent translation of the stent 12 and an engaged balloon angioplasty catheter 22 or other device engaged with the stent 12 on the guide wire 16 to the place of placement. Further as shown and described herein, once a first stent is placed appropriately in a blood vessel, the placement of adjacent stents 12 eliminating gaps therebetween is also achievable either by butting the second placed stent 12 against the first stent 12 or passing a smaller diameter stent 12 through the first placed stent 12 and engaging it on the distal end. Of course because the stents 12 all ride on the guide wire 16, it would be possible to position one stent 16 in a blood vessel 26 and not enlarge it, and then place one or more adjacent stents 12 abutting them or interlocking them as placed in a daisy chain. Once all in place, a balloon catheter with an elongated balloon could expand them all at once, locking them together and creating a gapless passageway from multiple abutted stents 12. Of course using the guide wire 16 to steer everything into place would also allow for conventional placement and enlargement one stent at a time.

FIG. 3 is a perspective view of a typical stent 12 with the guide wire 16 translating through the guide wire passage 14 omitting the conventional segmentation of the stent 12 for clarity, illustrating the location of marker bands 34 on the stiffening wire 36 and the markers 56 located on the stent 12, to be used by radiopaque marker system to aide the physician in manipulating both devices into proper position by providing a means for radiopaque location of both parts. The balloon angioplasty catheter 22 is shown in the expanded state to depict the internal cavity 58 that is filled with the saline solution or other inflation media through the inflation lumen port 60 of the inflation lumen 30.

FIG. 4 is an end view of a preferred embodiment of the herein disclosed stent 12, omitting the balloon angioplasty catheter 22, showing the guide wire passage 14 formed in a wall surface of the stent 12 on the exterior surface 62 of the stent 12. The centerline 64 of the guide wire passage 14 is substantially parallel to the center axis 66 of the stent central cavity 68.

FIG. 5 is an end view of another embodiment of the improved stent 12, omitting the balloon angioplasty catheter 22, showing the guide wire passage 14 formed in a sidewall of the stent 12 with half of the guide wire passage 14 protruding from the exterior of the stent 12 and half of the guide wire passage 14 protruding into the stent central cavity 68. Of course the amount of protrusion from the exterior of the stent 12 and into the stent central cavity 68 could be adjusted depending upon the intended use of the stent 12 and such is anticipated.

FIG. 6 depicts an end view of an additional preferred embodiment of the stent 12 with the guide wire passage 14 for translation on the guide wire 12 formed completely within the stent central cavity 68.

FIG. 7 is an end view of an additional preferred embodiment of the stent 12 which is compressed, omitting the balloon angioplasty catheter 22, so that the guide wire 16 is located on the guide wire passage 14 and is in a coaxial position with relation to the outer diameter of the stent 12. With the guide wire 16 in such a coaxial position, the stint 12 is more universally flexible in all directions, rather than when the guide wire passage 14 is on the outer edge of the stent 12, creating more resistance in one direction of bending than another.

FIG. 8 is an end view with the outer surface of the an alternate stent 70 embodiment omitting the balloon angioplasty catheter 22, and forming a guide wire passage 72 for translation on the guide wire 16 in a coaxial state. This embodiment of the device would form a guide wire passage 72 by flooding the sidewall forming the alternate stent 70 infernally into the stent central cavity 68. When this alternate stent 70 is expanded by the balloon angioplasty catheter 22, as shown in an expanded state in FIG. 9, the guide wire 16 becomes relocated to the outside surface of the alternate stent 70 with no guide wire passage 72.

FIG. 10 is an end view of bilateral external and internal segmentation 74 and 76 of the guide wire passage 14 with the external segmentation 74 and formed on the sidewall on the exterior surface 62 and the internal segmentation 76 opening into the stent central cavity 68. This embodiment could also be formed with a single external or internal segmentation 74 or 76 of the guide wire passage 14.

FIG. 11 is a perspective view of an embodiment of the disclosed stent 12 with a transversely segmented 78, guide wire passage 14.

FIG. 12 illustrates a means for engagement of adjacently placed stents 12 to eliminate gaps therebetween. As shown, a section through the sidewall overlapping of the internally relieved proximal end 80 of one stent 12 mates with and engages over the externally relieved sidewall of the distal end 82 of and adjacent second stent 42. Of course other means for engagement of the proximal end of one stent placed in a blood vessel with the distal end of an adjacently placed stent to eliminate gaps therebetween might be used, and such is anticipated; however in the current best mode of the device, an external relief on one stent 12 engaging an internal relief on the adjacent stent works best.

A means to lock two adjacent stents 12 placed in a blood vessel which would be an option in the current best embodiment of the device, is best depicted in FIG. 13. As shown, in a section through the sidewall of two adjacent stents 12, an interlocking between the two is achieved using the aforementioned relief engagement with the addition of engagement of the internally undercut 84 of the proximal end 80 of the first stent 12, with the externally undercut 86 of the distal end 82 of the second stent 42. Once expended, the second stent to be placed in the vessel would achieve a locked engagement with the first placed stent as well as a continuous sidewall that prevents any gap between the two adjacent stents. Of course, the guide wire passage 14 formed on or integral with the sidewall of the stent 12 would also be relieved to allow for the adjacent engagement of one or a plurality of stents 12 and alleviating gaps therebetween. This is best shown in FIG. 14 which is a perspective view of the guide wire passage 14 stepped in 88 on the distal end 82 of the second stent 42 and the guide wire passage 14 stepped out 90 on the proximal end 80 of the first stent 12 approaching a nesting position. This would allow for the gapless engagement between adjacent stents 12 as described as well as the lock engagement thereof is desired.

Figure 16:
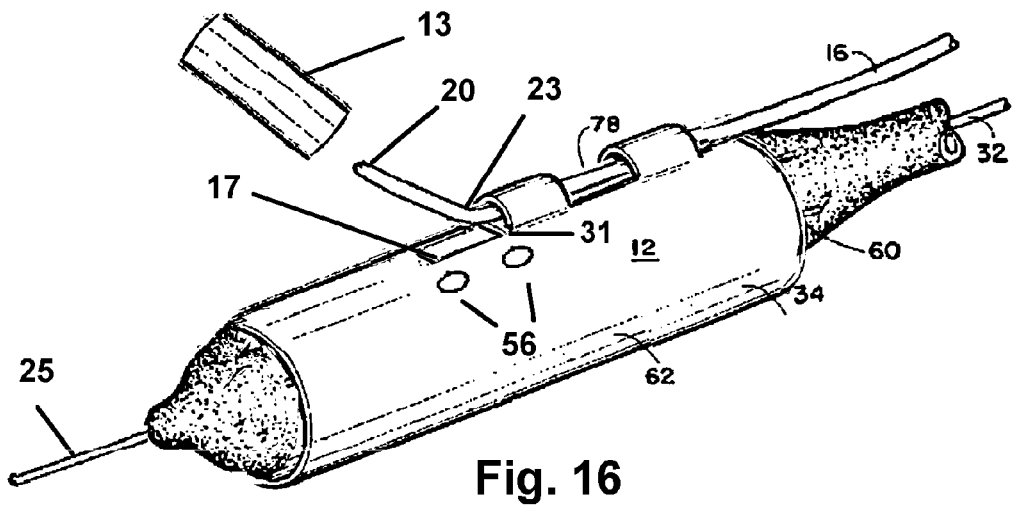
FIG. 16 shows another mode of the device the stent may be configured for engagement with a secondary stent located in an adjoining blood vessel, or aligned with that blood vessel using the curved distal end of the guide wire.

The device 10 herein is also configurable for deployment in a bifurcated configuration as shown in FIGS. 15 and 16. This type of deployment of stents 12 is particularly challenging in that the stent 12 is engaged in a first blood vessel and has a apertures that is aligned with an intersecting blood vessel. The aperture may also be employed to engage with a secondary stent 13 which is located in an intersecting blood vessel which communicates with the first blood vessel. The secondary stent 13, if employed, engaged with an aperture 17. Or the aperture 17 is aligned with the opening of the intersecting blood vessel and simply communicates blood or fluid through the aperture 17 with the flow in the blood vessel in which the stent 12 is located.

In the mode of the device in FIGS. 15-16, implantation is accomplished in a similar fashion to other modes of the device 10 noted earlier. In use, to position the stent 12, the physician employs the guide wire passage 14 to engage it upon the guide wire 16 and translate the stent 12 over the guide wire 16 through the arterial or venal system of the patient, to the guide wire distal end 20. The balloon angioplasty catheter 22 as shown, provides one means to laterally translate stent 12 with the guide wire 16 engaged through the guide wire passage 14 to the proper position.

In this mode of the device 10, the implant position would be at a point where the aperture 17 which communicates with the stent central cavity 68, is positioned inline with the intersecting blood vessel 27. During implantation, the curved distal end 20 of the guide wire 16 provides a means visually align the aperture 17 with the intersecting blood vessel. This function is provided by first threading the an angled portion extending from the distal end 20 of the guide wire 16 into the intersecting vessel 27. The departure point of the curve or angles portion from the transition point 23 of the guide wire 16, is such that when engaged in the intersecting vessel 27, it provides an alignment of the intersecting vessel 27 with the aperture 17.

In use the guide wire 16 is threaded through the main vessel 29 and the angled portion of the distal end 20 threaded into the intersecting vessel 27. Subsequently, the stent 12 is translated over the guide wire 16 until a termination point 31 in the formed wire passage 14 reaches transition point 23 or point along the guide wire 23 which substantially places the aperture 17 in line with the intersecting vessel 27.

Concurrently the user may also employ the markers 56 and the fixed extension wire 25 from the balloon catheter as a means to triangulate the location of the intersecting blood vessel and register it in engagement with the aperture 17. Further aiding proper placement is provided by positioning the extension wire 25 of the balloon catheter, extending axially forward of the intersecting vessel 27 to provide a visual means to ascertain the continuation of the main vessel 29 in which the stent 12 is located, past the intersection point in which the angled portion of the guide wire 16 extending from the transition point 23 is engaged. In use singularly or in combination, the two markers 56 would be aligned to center the straight extension portion of the guide wire 16, from the transition point 23 in-between the markers 56 thereby marking the location of the opening to the intersecting vessel in relation to the aperture 17 in between the markers 56.

Once properly aligned, the stent 12 will be enlarged and mounted in the main vessel 29 with the aperture 17 substantially aligned with the opening to the intersecting blood vessel 27. The communication of the intersecting vessel 27 with the aperture 17 provides a passage for blood flow between the central cavity 68 of the stent 12 and the interior of the intersecting vessel 27 in a bifurcated flow.

Optionally, a secondary stent 13 may be engaged with or communicating with the aperture 17. This would be handled by aligning the stent 12 in the aforementioned fashion using one or a plurality of the three means for such alignment. Once so aligned, the guide wire 16 may be retracted out of the wire passage 14 and translated into the central cavity 68 of the stent 12. Since the aperture 17 is aligned with the intersecting vessel 27 at this point, and the angled portion extending from the transition point 23 of the guide wire 16 is formed to align through the aperture 17 with the intersecting vessel 27, it will naturally move through the aperture 17 and into the aligned vessel 27. Thereafter, a collapsed secondary stent 13 may be translated along the guide wire 16 and into position in the intersecting vessel 27 and expanded using conventional expansion means such as a sheath that may be removed to allow instant expansion into the intersecting vessel 27.

While all of the fundamental characteristics and features of the present invention have been described herein, with reference to particular embodiments thereof, a latitude of modification, various changes and substitutions are intended in the foregoing disclosure and it will be apparent that in some instances, some features of the invention will be employed without a corresponding use of other features without departing from the scope of the invention as set forth. It should be understood that such substitutions, modifications, and variations may be made by those skilled in the art without departing from the spirit or scope of the invention. Consequently, all such modifications and variations are included within the scope of the invention as defined by the following claims.

What is claimed is:

1. An improved stent for implanting in a blood vessel comprising:
    an elongated stent, said sent having a first end and a second end, said stent having a sidewall defining a central cavity communicating between said first end and said second end;
    said central cavity having a center axis therethrough;
    a guide wire;
    a passageway formed axially along said sidewall in a unitary one-piece structure with said sidewall, said passageway having a diameter therethrough sized to accommodate lateral translation upon said guide wire, operatively engaged therein and communicating through a blood vessel;
    means to laterally translate said stent with said guide wire engaged through said passageway, to a determined position in said blood vessel of a patient;
    an aperture communicating through said sidewall adjacent to a termination point of said passageway between said first end and said second end;
    said guide wire having an angled portion at a distal end, said angled portion extending at an angle from an axis of said guide wire, from a first end of said angled portion located at an intersecting point on said guidewire, to said distal end opposite said first end;
    said angle of said angled portion formed to extend away from and align with, said aperture, when said stent is translated along said guide wire to a position with said intersecting point of said guide wire positioned adjacent to said termination point; and
    said angled portion, of said wire positionable by a translation thereof through said blood vessel, to extend from said first end at said intersecting point, to said distal end positioned within an intersecting second blood vessel, whereby said guide wire may be threaded into the blood vessel of a patient to a position where said angled portion becomes engaged in said intersecting second blood vessel, and said stent can be slid to said determined position where said aperture is aligned with said intersecting blood vessel by said angled portion defining means to align said aperture with said second blood vessel.

2. The improved stent for implanting in a blood vessel of claim 1, wherein said means to align said aperture with said intersecting second blood vessel additionally comprises:
    a pair of radiopaque markers positioned on said stent with said aperture centered therebetween.

3. The improved stent for implanting in a blood vessel of claim 1, wherein said means to align said aperture with said intersecting second blood vessel additionally comprises:
    said means to translate said stent along said guide wire being a balloon catheter; and
    a distal end of said balloon catheter having a fixed wire extending axially therefrom.

* * * * *